United States Patent
Lautenschlager et al.

(10) Patent No.: US 6,326,061 B1
(45) Date of Patent: Dec. 4, 2001

(54) AMINOSILOXANE POLYETHER POLYMERS

(75) Inventors: Hans-Jurgen Lautenschlager, Burghausen; Anton Heller, Simbach, both of (DE)

(73) Assignee: Wacker-Chemie GmbH, Munich (DE)

( * ) Notice: Subject to any disclaimer, the term of this patent is extended or adjusted under 35 U.S.C. 154(b) by 0 days.

(21) Appl. No.: 09/508,155

(22) PCT Filed: Aug. 27, 1998

(86) PCT No.: PCT/EP98/05443

§ 371 Date: Mar. 6, 2000

§ 102(e) Date: Mar. 6, 2000

(87) PCT Pub. No.: WO99/13151

PCT Pub. Date: Mar. 18, 1999

(30) Foreign Application Priority Data

Sep. 11, 1997 (DE) .............................. 197 39 991

(51) Int. Cl.$^7$ .............................. B05D 5/00; C08G 77/46; B32B 27/02
(52) U.S. Cl. .............................. 427/394; 528/29; 528/38; 556/444; 556/445; 442/59; 442/87; 427/387
(58) Field of Search .............................. 442/87, 59; 528/29, 528/38; 556/444, 445; 427/387, 394

(56) References Cited

U.S. PATENT DOCUMENTS

| | | |
|---|---|---|
| 4,036,868 | * 7/1977 | Atherton . |
| 5,075,403 | 12/1991 | Kirk . |
| 5,130,344 | 7/1992 | Kollmeier et al. . |
| 5,626,660 | 5/1997 | Lautenschlager et al. . |

FOREIGN PATENT DOCUMENTS

| | | |
|---|---|---|
| 39 28 867 C1 | 10/1990 | (DE) . |
| 0 404 698 A1 | 12/1990 | (EP) . |
| 0 579 999 A2 | 1/1994 | (EP) . |
| 0 692 567 A1 | 7/1995 | (EP) . |
| 0 728 813 A2 | 2/1996 | (EP) . |

OTHER PUBLICATIONS

English Derwent Abstract [MN 1996–070202[08]] Corresponding To EP 0 692 567 A1.

English Derwent Abstract Corresponding To EP 0 579 999 A2.

* cited by examiner

Primary Examiner—Robert Dawson
Assistant Examiner—Kuo-Liang Peng
(74) Attorney, Agent, or Firm—Brooks & Kushman P.C.

(57) ABSTRACT

Textiles treated with a textile treating composition containing a silane or organosiloxane containing both an Si—C bonded aminoalkyl group containing a primary, secondary, or tertiary amine group, and at least one Si—O—C bonded (iso) oxyalkyl radical exhibit excellent soft hand while maintaining superior water-wettability.

11 Claims, No Drawings

AMINOSILOXANE POLYETHER POLYMERS

The invention relates to a textile treatment process which uses a composition based on aminoalkyl- and (iso)oxyalkyl-containing organopolysiloxane and to novel aminosiloxane-polyether polymers.

A number of recent patents describe modifications to the polyoxyalkylene chain or to the organopolysiloxane for property optimization for a large number of applications. The functional groups and the polyoxyalkylene chains can be linked to the organopolysiloxane by way of Si—O—C or Si—C bonds.

DE 3928867 describes the use of polysiloxane-polyoxyalkylene block copolymers which comprise at least one amino-functional group attached to a silicon atom in the production of polyurethane foams. The polyoxyalkylene group and the amino-functional group can be attached via Si—O or Si—C. The polyoxyalkylene group and the amino-functional group can be located either at the ends or at the sides. The amino-functional group comprises at least two nitrogen atoms, of which that located at the end must be fully substituted by alkyl groups.

There is no description of polysiloxane-polyoxyalkylene block copolymers which comprise an amino-functional group attached to a silicon atom and have only one nitrogen atom, or of those which comprise two or more nitrogen atoms in the side chain and in which the terminal nitrogen atoms are substituted by at least one hydrogen atom. The use of the polymers described in DE 3928867 for fibre finishing is likewise not described.

U.S. Pat. No. 5,075,403 and EP-A-0404698 describe a poly-diorganosiloxane having amino and polyoxyalkylene side groups. The functional groups are attached via Si—C. Preparation is by hydrosilylation. The use of the polymers of the invention as wetting agent and dispersant or as additive in fabric softeners or antifoam powders is described.

Si—O—C-attached polyoxyalkylene groups are not described.

EP-A-0579999 describes a composition for defoaming an aqueous, especially alkaline, formulation based on organofunctionally modified organopolysiloxanes and finely divided silica. The organopolysiloxane used in the formulation is an amino siloxane whose amine groups are connected to the organopolysiloxane by way of Si—C or Si—O—C bond. In addition to the amine groups, the organopolysiloxane may also contain polyether radicals connected to the organopolysiloxane by way of Si—C or Si—O—C bond.

The combination of amino-functional and polyalkylene oxide-containing groups in the organopolysiloxane is also known. Alkylamine-polyalkylene oxidepolydimethylsiloxane terpolymers and polydimethylsiloxaneaminopolyalkylene oxide block copolymers have already been used for the finishing of textiles (cf. A. M. Czech et al., "Modified Silicone Softeners for Fluorocarbon Soil Release Treatments"). In that case the polyalkylene oxide groups are linked to the organopolysiloxane by way of Si—C bond.

A disadvantage of the prior art is that Si—C-bonded polyalkylene oxide groups are available only by way of the hydrosilylation reaction of allylpolyalkylene oxide groups on H-containing silanes and organopolysiloxanes. This process requires relatively expensive raw materials and special safety measures, since elimination of hydrogen must be expected in the case of hydrosilylation reactions. In addition, Si—C-bonded polyalkylene oxide groups cannot readily be eliminated on demand, as is desired in textile finishing in order to improve exhaustion capacity and permanence.

It is an object of the invention to overcome the disadvantages of the prior art.

A subject of the invention is a process for textile treatment in which a composition comprising at least one (A) silane or organosiloxane having at least one monovalent SiC-bonded radical with primary, secondary and/or tertiary amino groups and at least one (B) (iso)oxyalkyl radical which is attached via Si—O—C is used.

In the composition, preferably, the silane or organosiloxane (A) has a unit of the general formula (I)

and all other siloxane units in an organopolysiloxane have the general formula (II)

and have (iso)oxyalkyl radical of the formula $$(OC_nH_n(-R)_n)_o \qquad (III)$$

where
R can be identical or different and denotes hydrogen or a methyl radical.

The (iso)oxyalkyl radicals of the general formula $(OC_nH_n(-R)_n)_o$ can also be linked to the organopolysiloxane at one or both ends by way of Si—O—C bonds. The (iso)oxyalkyl radicals are preferably adducts of polyethylene oxide, polypropylene oxide and their copolymers. By altering the polyethylene oxide/polypropylene oxide ratio it is possible to influence the stability of the Si—O—C bond to hydrolysis.

$R^1$ denotes identical or different, monovalent, unsubstituted or fluorine-, chlorine- or bromine-substituted $C_1$ to $C_{18}$ hydrocarbon radicals, hydrogen atoms, $C_1$- to $C_{12}$-alkoxy or hydroxyl radicals or alkyl glycol radicals, Q denotes a group of the general formula (III)

where
$R^2$ denotes a divalent $C_1$ to $C_{18}$ hydrocarbon radical,
$R^3$ denotes a hydrogen atom or an unsubstituted or fluorine-, chlorine- or bromine- or $C_1$- to $C_5$-alkoxy-substituted $C_1$ to $C_{18}$ hydrocarbon radical,
a has the values 0, 1 or 2,
b has the values 1, 2 or 3,
c has the values 0, 1, 2 or 3,
d has the values 0, 1, 2, 3 or 4,
m has the values 2, 3, 4, 5 or 6,
n has the values 2, 3 or 4 and
o has the values from 1 to 100
and the sum of a and b is not more than 4.

Examples of $C_1$ to $C_{18}$ hydrocarbon radicals are alkyl radicals, such as the methyl, ethyl, n-propyl, isopropyl, n-butyl, isobutyl, tert-butyl, n-pentyl, isopentyl, neopentyl, tert-pentyl radical; hexyl radicals, such as the n-hexyl radical; heptyl radicals, such as the n-heptyl radical; octyl radicals, such as the n-octyl radical and isooctyl radicals, such as the 2,2,4-trimethylpentyl radical; nonyl radicals, such as the n-nonyl radical; decyl radicals, such as the n-decyl radical; dodecyl radicals, such as the n-dodecyl radical; cycloalkyl radicals, such as cyclopentyl, cyclohexyl, cycloheptyl radicals and methylcyclohexyl radicals; aryl radicals, such as the phenyl and the naphthyl radical; alkaryl radicals, such as o-, m-, p-tolyl radicals, xylyl radicals and ethylphenyl radicals; and aralkyl radicals, such as the benzyl radical, the alpha- or β-phenylethyl radical.

The above hydrocarbon radicals $R^1$ may comprise an aliphatic double bond. Examples are alkenyl radicals, such as the vinyl, allyl, 5-hexen-1-yl, E-4-hexen-1-yl, Z-4-hexen-1-yl, 2-(3-cyclohexenyl)ethyl and cyclododeca-4,8-dienyl radical. Preferred radicals $R^1$ with aliphatic double bond are the vinyl, allyl, and 5-hexen-1-yl radical.

Preferably, however, not more than 1% of the hydrocarbon radicals $R^1$ contain a double bond.

Examples of $C_1$ to $C_{18}$ hydrocarbon radicals substituted by fluorine, chlorine or bromine atoms are the 3,3,3-trifluoro-n-propyl radical, the 2,2,2,2',2',2'-hexafluoroisopropyl radical, the heptafluoroisopropyl radical, and the o-, m- and p-chlorophenyl radical.

Examples of the divalent $C_1$ to $C_{18}$ hydrocarbon radicals $R^2$ are saturated straight- or branched-chain or cyclic alkylene radicals such as the methylene and ethylene radical and also propylene, butylene, pentylene, hexylene, 2-methylpropylene, cyclohexylene and octadecylene radicals or unsaturated alkylene or arylene radicals such as the hexenylene radical and phenylene radicals, particular preference being given to the n-propylene radical and the 2-methylpropylene radical.

The alkoxy radicals are above-described alkyl radicals which are attached by way of an oxygen atom. The examples of alkyl radicals apply fully to the alkoxy radicals $R^1$ as well.

The alkyl glycol radicals $R^1$ preferably have the general formula (IV)

$$—R^2—[O(CHR^3)_d]_nOR^4 \qquad (IV)$$

in which $R^2$, $R^3$ and d have the above definitions, n has a value from 1 to 100 and $R^4$ denotes a hydrogen atom, a radical $R^3$ or a group of the general formula $—(C=O)—R^5$ where $R^5$ denotes the radical $R^3$ or $O—R^3$.

In the above general formulae (I) to (IV), preferably, $R^1$ denotes a methyl, phenyl, $C_1$- to $C_3$-alkoxy or hydroxyl radical or a radical of the general formula (IV), $R^2$ denotes a divalent $C_2$ to $C_6$ hydrocarbon radical, $R^3$ denotes a hydrogen atom, a methyl radical or cyclohexyl radical, a denotes the value 0 or 1, b denotes the value 1, c denotes the values 2 or 3, and d denotes the value 1.

Particular preference is given to linear polydimethylsiloxanes which may or may not have $C_1$- to $C_3$-alkoxy or hydroxyl end groups. In these polymethylsiloxanes, Q preferably denotes a group $H_2N(CH_2)_2NH(CH_2)_3$— or $H_2N(CH_2)_2NHCH_2CH(CH_3)CH_2$—.

A further subject of the invention is (A) silane or organosiloxane which has at least one monovalent SiC-bonded radical with primary, secondary and/or tertiary amino groups, with the proviso that the organopolysiloxane contains only M and D units and the amino-functional group located at the end has at least one hydrogen atom and at least one (B) (iso)oxyalkyl radical.

The (iso)oxyalkyl radicals of the general formula $(OC_nH_n(R)_n)_o$ can also be linked to the organopolysiloxane at one or both ends by way of Si—O—C bond. The (iso)oxyalkyl radicals are preferably adducts of polyethylene oxide, polypropylene oxide and copolymers thereof. By altering the polyethylene oxide/polypropylene oxide ratio it is possible to influence the stability of the Si—O—C bond to hydrolysis.

The ratio of the siloxane units of the general formula (I) to the siloxane units of the general formula (II) is preferably 1:10 to 30,000, especially 1:20 to 300.

The weight ratio of polyorganosiloxane to polyoxyalkylene groups is from 99:1 to 10:90, in particular from 95:5 to 30:70. The ratio of amino-substituted Si to total Si is preferably from 1:500 to 1:5, in particular from 1:200 to 20.

The amine contents of the composition of the invention are preferably from 0.1 to 2 mequiv/g, in particular from 0.1 to 0.7 mequiv/g, measured as the consumption of 1 N hydrochloric acid in ml/g of organopolysiloxane A in the course of titration to the neutral point.

It is possible to employ one type of silane or organosiloxane (A). It is alternatively possible to employ a mixture of at least two different types of silane and/or organosiloxane (A).

The silane or organosiloxane (A) or a mixture of at least two different types of silane and/or organosiloxanes (A) preferably has an average viscosity of from 1 to 100,000 mPa·s, in particular from 1 to 10,000 mPa·s, at 25° C.

A further subject of the invention is a process for preparing the compositions of the invention by using at least one (A) silane or organosiloxane having at least one monovalent, SiC-bonded radical with primary, secondary and/or tertiary amino groups and a glycol which has at least one (B) (iso)oxyalkyl radical.

The silanes or organosiloxanes (A) are prepared from (E) compounds selected from (E1) organosilanes having at least one monovalent SiC-bonded radical with primary, secondary and/or tertiary amino groups and at least one $C_1$- to $C_4$-alkoxy group and (E2) organosiloxanes having at least one monovalent SiC bonded radical with primary, secondary and/or tertiary amino groups and at least one $C_1$- to $C_4$-alkoxy and/or silanol group and (F) compounds selected from (F1) organosilanes having at least one $C_1$- to $C_4$-alkoxy group and (F2) organosiloxanes having at least one $C_1$- to $C_4$-alkoxy and/or silanol group, (G) glycols of the formula $$H(OC_nH_n(-R)_n)_oOH,$$

where

R=methyl or denotes H and also basic or acidic catalysts.

The organosilanes (E1) preferably have the general formula (VI)

$$Q_eR^6_fSiR^1_{(4-e-f)} \tag{VI}$$

in which $R^6$ is a $C_1$- or $C_2$-alkoxy radical, e denotes the values 1, 2 or 3, and f denotes the values 1, 2 or 3, with the proviso that the sum of e and f is not more than 4, and Q and $R^1$ have the above definitions.

The organosiloxanes (E2) preferably have at least one siloxane unit of the above general formula (I) and at least one siloxane unit of the general formula (VII)

$$R^1_g R^6_h R^7_i O_i SiO_{\frac{(4-g-h)}{2}}, \tag{VII}$$

and all other siloxane units have the above general formula (II), where g denotes the values 0, 1 or 2, h denotes the values 1, 2 or 3, and i denotes the values 0 or 1, with the proviso that the sum of g, h and i is not more than 3, and Q, $R^1$ and $R^6$ have the above definitions and $R^7$ represents H or a $C_1$- to $C_6$-alkyl group.

The organosilanes (F1) preferably have the general formula (VIII)

$$R^6_j SiR^1_{(4-j)} \tag{VIII}$$

in which j denotes the values 1, 2, 3 or 4 and $R^1$ and $R^6$ have the above definitions.

The organosiloxanes (F2) preferably have at least one siloxane unit of the above general formula (VII), and all other siloxane units of an organopolysiloxane have the above general formula (II).

Preferably, e denotes the value 1.

The organopolysiloxanes (E2) and (F2) preferably have an average viscosity of from 10 to 100,000 mPa·s, preferably from 20 to 10,000 mPa·s and, in particular, from 50 to 1000 mPa·s at 25° C.

The acidic catalysts are preferably Lewis acids such as $BF_3$, $MgCl_2$, and $ZnCl$, and proton-acidic compounds of the halogens, such as HF, HCl, HBr and HI, and sulphur-acidic compounds such as $H_2SO_4$ and $H_2SO_3$.

The basic catalysts are catalysts such as alkali metal hydroxides, especially sodium, potassium and caesium hydroxide, alkali metal alcoholates, quaternary ammonium hydroxides, such as tetramethylammonium hydroxide, benzyltrimethylammonium hydroxide, benzyltriethylammonium hydroxide, benzyltrimethylammonium butylate, β-hydroxyethyltrimethylammonium 2-ethylhexanoate, quaternary phosphonium hydroxides, such as tetra-n-butylphosphonium hydroxide and tri-n-butyl-3-[tris(trimethylsiloxy)silyl]-n-propylphosphonium hydroxide, alkali metal siloxanolates and ammonium organosiloxanolates, such as benzyltrimethylammonium siloxanolate and tetramethylammonium siloxanolate.

Use is made preferably of from 10 ppm to 1% by weight, in particular from 50 to 1000 ppm, of catalyst, based in each case on the weight of the organosilicon compounds employed.

The amounts (E), (F) and (G) result from the required physical data.

Products containing acyl groups can be prepared by using acylated amino-functional silanes or by reacting the aminopolyoxyalkylenesiloxane of the invention with acylating reagents, such as carboxylic anhydrides, carboxylic esters, carboxylic acids, lactones and carbonates.

The preparation of (A) takes place preferably at temperatures from 50 to 300° C., in particular from 80 to 200° C.

The reaction time within which 99 mol-% of the starting compounds (E), (F) and (G) are reacted to silane or organosiloxane (A) is in most cases from 1 hour to 20 days, in particular from 12 hours to 3 days.

In order to avoid reverse reactions it is important in the course of the preparation to remove from the reaction mixture all elimination products, such as water, alcohol and ethers.

The textile treatment formulations of the invention comprise preferably (A) silane or organosiloxane in amounts of from 1 to 60% by weight, more preferably from 1 to 30% by weight, and water in amounts from 40 to 99% by weight.

The compounds of the invention can be used as compositions for the treatment of leather, bonded web fabrics, cellulose, fibres, textiles, nonwovens and tissues, as a constituent of antifoam formulations, as wetting agents, as a coatings additive and as a stabilizer for PU foam.

Advantages are the very good slip effect and outstanding softness coupled with very good hydrophilicity, depending on composition, easily emulsifiable —self-dispersing— soluble in water, depending on composition, high liquor compatibility, surprising stability to hydrolysis for forced application from aqueous liquor, and good exhaustion capacity as a result of targeted partial hydrolysis of the Si—O—C bonds. Furthermore, the compositions of the invention have a good stability which may amount to years. In addition, the stability can also be adjusted through the targeted choice of the glycol and of the pH, the pH preferably lying at from 7 to 9.

PREPARATION EXAMPLE 1

693.75 g of an OH-terminal polydimethylsiloxane having a viscosity of 50 mPa·s are mixed with 21.38 g of aminoethylaminopropylmethyldimethoxysilane, 358.07 g of polyethylene glycol 400 and a basic catalyst. The result is a turbid whitish mixture. The mixture is heated gradually to 200° C. with stirring, in the course of which volatile constituents are removed by applying reduced pressure. The result is the clear to slightly turbid oil 1 having a viscosity of 430 mPa·s and a amine number of 0.23.

PREPARATION EXAMPLE 2

693.75 g of an OH-terminal polydimethylsiloxane having a viscosity of 50 mPa·s are mixed with 21.38 g of aminoethylaminopropylmethyldimethoxysilane, 358.07 g of polyethylene glycol 400 and a basic catalyst. The result is a turbid whitish mixture. The mixture is heated gradually to 200° C. with stirring, in the course of which volatile constituents are removed by applying reduced pressure. After cooling to 60° C. and aeration, 10.10 g of succinic anhydride are added to the oil. After 90 minutes the yellow oil 2 is obtained, having a viscosity of 702 mPa·s and an amine number of 0.12.

PREPARATION EXAMPLE 3

555.00 g of an OH-terminal polydimethylsiloxane having a viscosity of 50 mPa·s are mixed with 17.10 g of aminoethylaminopropylmethyldimethoxysilane, 573.60 g of polyethylene glycol 400 and a basic catalyst. The result is a turbid whitish mixture. The mixture is heated gradually to 200° C. with stirring, in the course of which volatile constituents are removed by applying reduced pressure. The result is the clear to slightly turbid oil 3 having a viscosity of 209 mPa·s and a amine number of 0.17.

PREPARATION EXAMPLE 4

555.00 g of an OH-terminal polydimethylsiloxane having a viscosity of 50 mPa·s are mixed with 17.10 g of aminoethylaminopropylmethyldimethoxysilane, 573.60 g of polyethylene glycol 400 and a basic catalyst. The result is a turbid whitish mixture. The mixture is heated gradually to 200° C. with stirring, in the course of which volatile constituents are removed by applying reduced pressure. After cooling to 60° C. and aeration, 8.00 g of succinic anhydride are added to the oil. After 90 minutes the yellow oil 4 is obtained, having a viscosity of 249 mpa·s and an amine number of 0.09.

COMPARATIVE EXAMPLE

EXAMPLE 5

A mixture of 967 g of OH-terminal polydimethylsiloxane having a viscosity of about 70 mpa·s at 25° C., 33 g of aminoethylaminopropyldimethoxymethylsilane and a 40% strength solution of a quaternary ammonium hydroxide in methanol is heated at 80° C. under nitrogen and with stirring for 4 hours. The quaternary ammonium hydroxide is then deactivated by heating at 150° C. for 60 minutes and applying reduced pressure and at the same time the organopolysiloxane is freed from constituents which boil under these conditions. The resulting organopolysiloxane has a viscosity of 1000 mPa·s at 25° C. and a titratable amine content of 0.3 ml of 1 N HCl/g of solids (oil 5).

USE EXAMPLE (UE)

20 parts of oil 1 are stirred in 80 parts of water which has been acidified to a pH of 3 with acetic acid. A slightly turbid dispersion is obtained (UE1).

20 parts of oil 2 are stirred in 80 parts of water. A slightly turbid dispersion is obtained (UE2).

20 parts of oil 3 are stirred in 80 parts of water which has been acidified to a pH of 3 with acetic acid. A clear solution is obtained (UE3).

20 parts of oil 4 are stirred in 80 parts of water. A clear solution is obtained (UE4).

4 parts of the emulsifier Genapol X060 (from Hoechst AG) and 4 parts of water are mixed homogeneously. 20 parts of oil 5 are then incorporated slowly and in portions. Using 74.5 parts of water the homogeneous mixture is diluted, slowly at first and then rapidly. The emulsion is filtered through fine Perlon fabric. Subsequently, 1.5 parts of acetic acid (concentrated) are added to the emulsion (UE5).

50 g each of UE1 to UE5 are mixed with 950 g of deionized water. Polyester/cotton fabric (poly/cotton) (65:35) is immersed thoroughly in each mixture and squeezed off on a pad mangle (30 kg load). The poly/cotton fabrics F1 to F5 are dried at 150° C. for 5 minutes.

The hand is evaluated in accordance with a relative scale from 0–10, where the value 10 represents the best soft hand in each case.

The hydrophilicity of the fabric is defined by the time, measured in seconds, for one drop of water a) to start to wet the fabric and b) to be absorbed completely by the fabric.

| Fabric | Soft hand | Hydrophilicity | |
|---|---|---|---|
| | | Time to start of wetting [s] | Absorption time [s] |
| F1 | 8 | 1 | 7 |
| F2 | 8 | 1 | 6 |
| F3 | 6 | 1 | 3 |
| F4 | 6 | 1 | 3 |
| F5 | 10 | 50 | 156 |
| Blank value | 0 | 1 | 5 |

The result shows that the silicones oil 1 to oil 4 of the invention maintain outstandingly the absorbency of the fabrics treated with them and at the same give them a very good soft hand.

What is claimed is:

1. A process for textile treatment comprising contacting a textile material with a composition comprising at least one
   (A) silane or organosiloxane having at least one monovalent SiC-bonded hydrocarbon radical having primary, secondary and/or tertiary amino groups, and at least one
   (B) (iso)oxyalkyl radical which is attached to said silane or organosiloxane (A) via Si—O—C bonding, wherein the textile material is not rendered hydrophobic by said contacting with said silane or said organopolysiloxane.

2. The process of claim 1, wherein the (iso)oxyalkyl radical (B) is $(OC_nH_n(-R))_o$, where
   R can be identical or different and denotes hydrogen or a methyl radical,
   n is 2, 3 or 4 and
   o is from 1 to 100.

3. The process of claim 1, in which the silane or organosiloxane (A) contains at least one siloxane unit of the general formula (I)

$$R^1_a Q_b SiO_{\frac{(4-a-b)}{2}} \quad (I)$$

and all other siloxane units have the general formula (II)

 (II)

where

R$^1$ denotes identical or different monovalent, unsubstituted or fluorine-, chlorine- or bromine-substituted C$_1$ to C$_{18}$ hydrocarbon radicals, hydrogen atoms, C$_1$- to C$_2$-alkoxy radicals, hydroxyl radicals, or alkyl glycol radicals, Q denotes a group of the general formula (III)

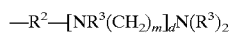 (III)

where

R$^2$ denotes a divalent C$_1$ to C$_{18}$ hydrocarbon radical,

R$^3$ denotes a hydrogen atom or an unsubstituted or fluorine-, chlorine- or bromine- or C$_1$- to C$_5$-alkoxy-substituted C$_1$ to C$_{18}$ hydrocarbon radical, a is 0, 1 or 2, b is 1, 2 or 3, c is 0, 1, 2 or 3, d is 0, 1, 2, 3 or 4, m is 2, 3, 4, 5 or 6, and the sum of a and b is not more than 4.

4. The process of claim 2, in which the silane or organosiloxane (A) contains at least one siloxane unit of the general formula (I)

 (I)

and all other siloxane units have the general formula (II)

 (II)

where

R$^1$ denotes identical or different monovalent, unsubstituted or fluorine-, chlorine- or bromine-substituted C$_1$ to C$_{18}$ hydrocarbon radicals, hydrogen atoms, C$_1$- to C$_{12}$-alkoxy radicals, hydroxyl radicals, or alkyl glycol radicals, Q denotes a group of the general formula (III)

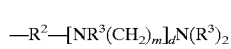 (III)

where

R$^2$ denotes a divalent C$_1$ to C$_{18}$ hydrocarbon radical,

R$^3$ denotes a hydrogen atom or an unsubstituted or fluorine-, chlorine- or bromine- or C$_1$- to C$_5$-alkoxy-substituted C$_1$ to C$_{18}$ hydrocarbon radical, a is 0, 1 or 2, b is 1, 2 or 3, c is 0, 1, 2 or 3, d is 0, 1, 2, 3 or 4, m is 2, 3, 4, 5 or 6, and the sum of a and b is not more than 4.

5. The process of claim 1, in which the amine content of the composition is from 0.01 to 2 meq/g, measured as the consumption of 1 N hydrochloric acid in ml/g by the composition (A) and (B) on titration to the neutral point.

6. The process of claim 3, in which the amine content of the composition is from 0.01 to 2 meq/g, measured as the consumption of 1 N hydrochloric acid in ml/g by the composition (A) and (B) on titration to the neutral point.

7. The process of claim 4, in which the amine content of the composition is from 0.01 to 2 meq/g, measured as the consumption of 1 N hydrochloric acid in ml/g by the composition (A) and (B) on titration to the neutral point.

8. A process for preparing the composition of claim 1, by reacting at least one (A) silane or organosiloxane which has at least one monovalent SiC-bonded radical with primary, secondary and/or tertiary amino groups, with a glycol which has at least one (B) (iso)oxyalkyl radical.

9. A process for preparing the composition of claim 2, by reacting at least one (A) silane or organosiloxane which has at least one monovalent SiC-bonded radical with primary, secondary and/or tertiary amino groups, with a glycol which has at least one (B) (iso)oxyalkyl radical.

10. A process for preparing the composition of claim 3, by reacting at least one (A) silane or organosiloxane which has at least one monovalent SiC-bonded radical with primary, secondary and/or tertiary amino groups, with a glycol which has at least one (B) (iso)oxyalkyl radical.

11. A process for preparing the composition of claim 4, by reacting at least one (A) silane or organosiloxane which has at least one monovalent SiC-bonded radical with primary, secondary and/or tertiary amino groups, with a glycol which has at least one (B) (iso)oxyalkyl radical.

* * * * *